United States Patent
Parsons et al.

(10) Patent No.: US 7,014,871 B1
(45) Date of Patent: Mar. 21, 2006

(54) IODINE PREPARATION COMPOSITION

(75) Inventors: Dave Parsons, Heswall (GB);
Elizabeth Jacques, Chester (GB);
Philip Bowler, Warrington (GB)

(73) Assignee: Bristol-Myers Squibb Company

( * ) Notice: Subject to any disclaimer, the term of this patent is extended or adjusted under 35 U.S.C. 154(b) by 0 days.

(21) Appl. No.: 09/936,421

(22) PCT Filed: Mar. 13, 2000

(86) PCT No.: PCT/EP00/02194

§ 371 (c)(1),
(2), (4) Date: Jan. 7, 2002

(87) PCT Pub. No.: WO00/54593

PCT Pub. Date: Sep. 21, 2000

(30) Foreign Application Priority Data

Mar. 12, 1999 (GB) .................................... 9905663

(51) Int. Cl.
| | |
|---|---|
| *A61K 33/18* | (2006.01) |
| *A01N 59/12* | (2006.01) |
| *A61P 17/02* | (2006.01) |
| *A61K 33/40* | (2006.01) |
| *A61K 33/20* | (2006.01) |
| *A01N 59/00* | (2006.01) |

(52) U.S. Cl. ...................... 424/668; 424/613; 424/614; 424/615; 424/616; 424/639; 424/640; 424/661; 424/662; 424/665; 424/667; 424/669; 424/670; 424/671; 424/723; 424/DIG. 13; 514/887; 514/964

(58) Field of Classification Search ........ 424/613–616, 424/639–640, 661–662, 665, 667–671, 723, 424/DIG. 13; 514/887, 964
See application file for complete search history.

(56) References Cited

U.S. PATENT DOCUMENTS 4,271,149 A  *  6/1981  Winicov ..................... 424/150
5,128,136 A        7/1992  Bentley et al.

FOREIGN PATENT DOCUMENTS

| WO | 2276549 | 10/1994 |
|---|---|---|
| WO | WO9512316 | 5/1995 |
| WO | WO9965538 | 12/1999 |

OTHER PUBLICATIONS

Martindale The Extra Pharmacopoeia, The Pharmaceutical Press, London, 1993, pp. 972-973.*

* cited by examiner

*Primary Examiner*—John Pak
(74) *Attorney, Agent, or Firm*—John M. Kilcoyne

(57) ABSTRACT

An iodine preparation composition suitable for use on wounds comprising an iodide source, an oxidant and a buffer characterized in that the iodide is held separately from the oxidant until the point of use, and that the buffer is capable of maintaining the pH of the composition at between pH 45 and pH 6 so that iodine is generated at a physiologically acceptable dose rate.

6 Claims, No Drawings

IODINE PREPARATION COMPOSITION

This invention relates to an antimicrobial composition which can be applied to wounds, cuts, abrasions or burns for the prevention or treatment of infections. More particularly the invention relates to a composition capable of providing effective antimicrobial activity while at the same time avoiding wound and skin irritation and retardation of wound healing.

Topical antimicrobial materials and preparations containing them have long been recognised as important parts of antisepsis of intact skin and wounds. Iodine has been recognized as an antimicrobial agent with effectiveness against a wide range of micro-organisms. There are however several barriers to making an effective antimicrobial composition for application to wounds based on iodine. One problem is that iodine tends to react with organic materials found in the wound other than the intended microbial targets. This means that to be effective, iodine needs to be included at high levels such as 0.9% by weight, as described in "Handbook of Wound Dressings" edited by Stephen Thomas, 1994 Journal of Wound Care. At such levels and with continued use iodine may have undesirable local side effects such as cell toxicity, hypersensitivity reactions, skin staining, and unpleasant odour and systemic adverse effects such as metabolic acidosis and impairment of renal function. For this reason application of iodine is recommended at levels below 1.35 g in one week.

A further problem is that iodine has a relatively short shelf life when in aqueous solution meaning either that compositions which include water need to be freshly prepared before each application or again that iodine is included at high levels. These factors limit product form.

In the past these problems with iodine have sought to be addressed by the use of iodophors which act as a release mechanism for iodine. Iodophors are readily dissociable, loose complexes of iodine with polymers or surfactants. Iodophor compositions are not best suited to use on wounds because when applied to a wound, all iodine present in the composition is readily available for reaction and therefore the adverse reactions associated with high levels of iodine are not necessarily avoided.

There thus exists a need for a composition which delivers iodine to a wound at a rate which is high enough to provide effective antisepsis but which is low enough to avoid the problems of adverse reactions associated with high levels of iodine.

GB-B-2276546 to Diversey relates to improved iodophors which are prepared at the point of use. The composition comprises an iodide source, an oxidant and an acid source, the oxidant becoming active only when the composition is dissolved in an aqueous medium. The composition is said to overcome the stability problems associated with producing teat dip/spray iodine formulations for use in the control of bovine mastitis. The rate of generation of iodine needed for these topical formulations for use on intact skin far exceeds that tolerable to a wound. In these compositions such high levels of iodine are generated that a hydrotrope must be included to prevent the iodine from crystallising. In addition, iodine has a complex chemistry in aqueous solutions and exists in a number of equilibria. At high iodine concentrations in the presence of iodide there is a strong tendency for the tri-iodide ion to form. We believe that this ion has very little antimicrobial activity but can still be absorbed with the risk of systemic toxicity.

We have found that it is possible to prepare a composition which is capable of generating iodine at a rate and level that makes it suitable for use in wounds. This is achieved by separating certain of the ingredients and controlling the kinetics of the generation of iodine through the manipulation of pH.

Accordingly the present invention provides an iodine preparation composition suitable for use on wounds comprising an iodide source, an oxidant and a buffer characterised in that the oxidant is held separately from the iodide until the point of use, and that the buffer is capable of maintaining the pH of the composition at between pH 4.5 and pH 6 so that iodine is generated at a physiologically acceptable and efficacious rate.

The invention allows the preparation of compositions generating a low but effective iodine level for example up to about 2000 µg per g of composition per hour, preferably in the range of 5 µg per g of composition per hour to 1500 µg per g of composition per hour, more preferably in the range 50 µg per g of composition per hour to 1000 µg per g of composition per hour so that the amount of free iodine available for antisepsis at any time is at least 0.001%.

The compositions of the invention are preferably formulated to generate the above levels of iodine over a period of about 3 days.

The pH of the composition of the invention is generally below 5.8. We have found that if the pH is greater than about 6, the rate of production of iodine by reaction of the oxidising agent with iodide ions is too low to balance any losses of iodine by reaction with the organic matter. We have found that it is generally desired that the pH of the compositions is not below about 4.5 as otherwise there is a danger that the rate of oxidation of the iodide ions will be too fast with the result that the composition could become toxic.

The desired pH of the compositions may be achieved by incorporating buffering agents therein. Examples of buffering agents which may be included are citric acid/disodium hydrogen phosphate, citric acid/sodium citrate, acetic acid/sodium acetate. The buffering agent may conveniently be present in an amount of about 2% to 10%, preferably about 4% to 6% by weight and particularly about 5% by weight so as to provide an isotonic composition.

The amount of oxidant in the composition is tailored to provide a stoichiometric match with iodide. Preferably the oxidant is iodate and is provided in a molar ratio of 1:5 with iodide. In this way the iodide present in the composition fully reacts with all the oxidant. To provide the levels and rate of production of iodine in the range described above it is desirable to include up to 2% by weight of iodide, preferably, from 0.2% to 2% by weight of iodide. Iodide and iodate are preferably present as sodium salts although other usual counter ions may be used.

Convenient forms of administration of the composition include aqueous gels, films, creams, tablets and capsules.

The following examples are illustrative of the present invention.

EXAMPLE 1

| Gel A | Weight g |
| --- | --- |
| Hydroxyethyl cellulose | 30.00 |
| Propylene Glycol | 150.00 |
| $Na_2HPO_4$ | 35.61 |
| Citric Acid | 21.01 |

-continued

| | |
|---|---|
| Potassium Iodate | 1.124 |
| Water | 762.256 |

| Gel B | Weight in g |
|---|---|
| Hydroxyethyl cellulose | 30.0 |
| Propylene Glycol | 150.0 |
| Potassium Iodide | 4.36 |
| Water | 815.64 |

Gel A was made by dissolving the buffer salt in a water/propylene glycol mix and then adding the iodate. When the solution is clear the hydroxyethyl cellulose is added and mixed until gelation is complete. Gel B was made by dissolving iodide in a water/propylene glycol mix. Hydroxyethyl cellulose was added to this mixture and mixed until gelation was complete.

The gels were packaged in separate syringes which were bound together with their nozzles fitted into a Y-shaped connecter. The contents were sterilised by autoclaving at 121 C for 15 minutes. Simultaneous depression of the plungers allows the gels to be co-extruded and allows the gels to react while being dispensed into a wound. The co-extrusion of the gels results in a product producing approximately 100 μg per g of composition per hour at a pH of about 5.4. The composition generated a greater than 5 log kill of *S. aureous* (NCIMB 9518) which is regarded as being an acceptable level of antimicrobial activity.

EXAMPLE 2

| Film A | g |
|---|---|
| Hydroxypropylcellulose | 16 |
| Propylene Glycol | 4 |
| Potassium Iodate | 0.1124 |
| Sodium phosphate | 1.7805 |
| Citric acid | 1.0505 |
| Water | 77.0566 |

| Film B | |
|---|---|
| Hydroxypropylcellulose | 16 |
| Propylene Glycol | 4 |

-continued

| | |
|---|---|
| Potassium Iodide | 0.436 |
| Water | 79.564 |

The films are produced by knife over roller coating of aqueous solution onto an inert carrier followed by drying at a temperature not exceeding 100 C and sterilised by gamma irradiation.

The films may be cut into rectangles and added to a wound whereupon they dissolve in the wound fluid and reaction takes place.

The invention claimed is:

1. An iodine preparation suitable for use on wounds comprising:
   (A) a first part comprising an iodide source; and
   (B) a second part comprising an oxidant and a buffer;
   wherein (1) said first part and said second part are combined at the point of use, (2) when said first part and said second part are combined, the iodide source is present in an amount that is 0.2 to 2 wt % of the combined two parts, (3) when said first part and said second part are combined at the point of use, the buffer maintains the pH of the combined two parts at between 4.5 and 6, and (4) when said first part and said second part are combined at the point of use, iodine is generated at a rate of 5 to 1500 micrograms per one gram of the combined two parts per hour.

2. The iodine preparation as claimed in claim 1 characterized in that the combined iodide source, oxidant and buffer generates 100 μg of iodine per g of combination per hour.

3. The iodine preparation as claimed in claim 1 formulated so that the combined iodide source, oxidant and buffer generates the said levels of iodine over a period of three days.

4. The iodine preparation as claimed in claim 1 wherein the pH of the combined iodide source, oxidant and buffer is maintained between about 5.4 and 5.8.

5. A method of treating a wound comprising applying to said wound an effective wound treating amount of an iodine preparation as claimed in claim 1.

6. A method of treating sepsis in wounds comprising applying to said wound an effective sepsis treating amount of an iodine preparation as claimed in claim 1.

* * * * *